(12) United States Patent
Eguchi et al.

(10) Patent No.: US 6,569,652 B1
(45) Date of Patent: May 27, 2003

(54) PROCESS FOR PREPARING OPTICALLY ACTIVE 1,2-DIOLS

(75) Inventors: Tamotsu Eguchi, Tokyo (JP); Hideyo Kumazawa, Tokyo (JP); Kenichi Mochida, Kanagawa (JP)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/486,442

(22) PCT Filed: Aug. 27, 1997

(86) PCT No.: PCT/JP97/02986
§ 371 (c)(1),
(2), (4) Date: Feb. 25, 2000

(87) PCT Pub. No.: WO99/10518
PCT Pub. Date: Mar. 4, 1999

(51) Int. Cl.$^7$ ................................................ C12P 13/02
(52) U.S. Cl. ........................ 435/129; 435/280; 435/156
(58) Field of Search ................................ 435/129, 156, 435/280

(56) References Cited

U.S. PATENT DOCUMENTS

| | | |
|---|---|---|
| 5,824,540 A | 10/1998 | Connors |
| 5,858,737 A | 1/1999 | Buckland et al. |
| 5,871,981 A | 2/1999 | Chartrain et al. |

OTHER PUBLICATIONS

Allen et al., "Metabolism of Napththalene, 1–Naphthol, Indene and Indole by Rhodococcus sp. Strain NCIMB 12038", Applied and Environmental Microbiology 63 (1) : 151–55 (Jan. 1997).*
Wen et al., "Induction of a cytochrome P450–dependent fatty acid monooygenase in *Bacillus megaterium* by a barbiturate analog", Mol. Cell. Biochem 67 (1) : 77–81 (1985).*
ATCC Bacteria and Bacteriophages, 19th Edition, p. 303 (1996).*
H. L. Holland, "Side Chain Hydroxylation of Aromatic Compounds by Fungi. Part 6. Biotransformation of Olefins by *Mortierella Isabellina*", Biocatalysis, 1994, vol. 10, pp. 65–76.
R. Agarwal et al., "Chemical and Enzyme–Catalyzed Synthesis of Quinoline Arene Hydrates", Bioorganic & Medicinal Chemistry, 1994, vol. 2, No. 6, pp. 439–446.
T. A. Lyle et al., "Benzocycloalkyl Amines as Novel C–Termini for HIV Protease Inhibitors", J. Med. Chem., 1991, vol. 34, pp. 1228–1230.
D. R. Boyd et al., "Stereospecific Benzylic Hydoxylation of Bicyclic Alkenes by *Pseudomonas putida*: Isolation of (+)–R–1–Hydroxy–1,2–dihydronaphthalene, an Arene Hydrate of Naphthalene form Metabolism of 1,2 Dihydronaphthalene", J. Chem. Soc., Chem. Commun., 1989, pp. 339–340.

C. C. R. Allen et al., "Enantioselective Bacterial Biotransformation Routes to cis–Diol Metabolites of Monosubstituted Benzenes, Naphthalene and Benzocycloalkenes of Either Absolute Configuration", J. Chem. Soc., Chem. Commun., 1995, pp. 117–118.

M. Imuta et al., "Synthesis and Absolute Stereochemistry of cis–and trans–1,2–Indandiols: Metabolites of Indene and 2–Indanone", J. Org. Chem., 1978, vol. 43, No. 23, pp. 4540–4542.

M. Kasai et al., "Enantioselective Ester Hydrolyses Employing *Rhizopus nigricans*. A Method of Preparing and Assigning the Absolute Stereochemistry of Cyclic Alcohols", J. Org. Chem., 1984, vol. 49, pp. 675–679.

D. R. Boyd., "Chemical Synthesis and Optical Purity Determination of Optically Active 1,2–Epoxyindan and Alcohol Products which are also derived from Mammalin and Microbial Metabolism of Indene or Indanones", J. Chem. Soc. Perkins Trans. I, 1982, pp. 2767–2770.

J. E. Taylor, "Catalytic cis to trans Conversions; Dihydroxybicyclo[2.2.1]heptane and 1,2–Dihydroxyindane", Synthesis, 1985, pp. 1142–1144.

(List continued on next page.)

Primary Examiner—Irene Marx
(74) Attorney, Agent, or Firm—Kenneth R. Walton; Melvin Winokur

(57) ABSTRACT

The present invention relates to a process for producing optically active diols represented by the general formula (II):

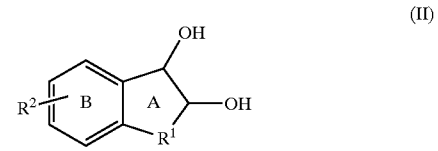

(II)

wherein $R^1$ represents $(CH_2)_n$, $CH=CH$, O, S or NH whereupon n is an integer of 1 to 4, and $R^2$ represents hydrogen, $C_{1-6}$ alkyl, $C_{1-6}$ alkoxy, ($C_{1-6}$ alkoxy)-carbonyl, hydroxy, carboxy, halogen, nitro or amino, which comprises treating compounds represented by the general formula (I):

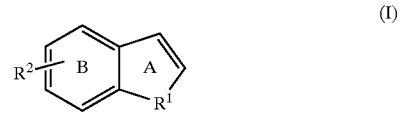

(I)

wherein $R^1$ and $R^2$ have the same meanings as defined above, with a culture of a microorganism belonging to the genus Rhodococcus, Bacillus, Brevibacterium or Gordona and being capable of stereoselectively diolating a double bond in ring A, or with a culture of *Mortierella vinacea*, or with said microorganism itself, or with a treated material from said microorganism.

15 Claims, No Drawings

OTHER PUBLICATIONS

D. T. Gibson et al., "Biotransformations Catalyzed by Toluene Dioxygenase from *Pseudomonas putida* F1", Amer. Soc. for Microbiology, 1990, pp. 121–133.

D. T. Gibson et al., "Oxidative Degradation of Aromatic Hydrocarbons by Microorganisms. I. Enzymatic Formation of Caechol from Benzene", Biochemistry, 1968, vol. 7(7), pp. 2653–2662.

L. P. Wackett et al., "Benzylic Monooxygenation Catalyzed by Toluene Dioxygenase from *Pseudomonas putida*", 1988, Biochemistry, vol. 27, pp. 1360–1367.

A. M. Warhurst et al., "Biotransformations Catalyzed by the Genus Rhodococcus", 1994, Critical Reviews in Biotechnology, vol. 14(1), pp. 29–73.

* cited by examiner

PROCESS FOR PREPARING OPTICALLY ACTIVE 1,2-DIOLS

TECHNICAL FIELD

The present invention relates to a process for producing optically active 1,2-diols.

The optically active 1,2-diols are useful as various pharmaceutical preparations and optically active, biologically active substances, as well as intermediates of their derivatives.

For example, cis-(1S,2R)-dihydroxyindane or trans-(1R,2R)-dihydroxyindane can be an important starting material of Crixivan used as an anti-AIDS drug because of its inhibitor activity on proteolytic enzymes for AIDS virus (J. Med. Chem., 34, 1228 (1991)).

BACKGROUND ART

Known methods of microbially producing optically active 1,2-diols include, for example, a method of reacting indene along with a cultured microorganism of the genus Pseudomonas (J. Chem. Soc., Chem. Commun., 339 (1989); J. Chem. Soc., Chem. Commun., 117 (1995)), a method of adding a derivative such as indene, 1,2-dihydronaphthalene or the like to a culture of *Mortierella isabellina* to convert it into a hydroxide (Bioorg. Med. Chem., 2, 439 (1994)), a method of using as a starting material optically active 2-bromo-1-hydroxyindane generated upon asymmetrical reduction of 2-bromoindane-1-one with *Cryptococcus macerans* (J. Org. Chem., 43, 4540 (1978)), and a method of stereoselectively hydrolyzing 1-methoxy-2-acetoxyindane in a culture of *Rhizopus nigricans* (J. Org. Chem., 49, 675 (1984)).

Further, known methods of synthesizing optically active 1,2-dihydroxyindane derivatives by chemical synthesis include a method of reacting 2-bromo-1-hydroxyindane in the presence of acetic acid or acetic acid and water (J. Chem. Soc. Perkin Trans. I., 2767 (1982)) and a method of oxidatively hydrating indene (Synthesis, 1142 (1985)).

However, these conventional methods, particularly chemical synthetic methods, have the problems that the starting materials are expensive, the operation is cumbersome and the yield is low because of the multiple-step reaction, or the optical purity of the resulting 1,2-dihydroxyindane is low, while the microbial methods also have the problem that the range of utilizable microorganisms is limited.

DISCLOSURE OF THE INVENTION

The object of the present invention is to provide a process for producing optically active 1,2-diols efficiently by microorganisms not used in the conventional microbial methods.

That is, the present invention encompasses:
1. A process for producing optically active diols represented by the general formula (II):

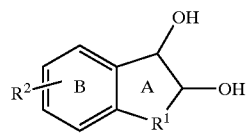

(II)

wherein $R^1$ represents $(CH_2)_n$, CH=CH, O, S or NH whereupon n is an integer of 1 to 4, and $R^2$ represents hydrogen, $C_{1-6}$ alkyl, $C_{1-6}$ alkoxy, $C_{1-6}$ alkoxy-carbonyl, hydroxy, carboxy, halogen, nitro or amino, which comprises treating compounds represented by the general formula (I):

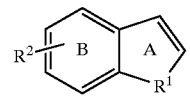

(I)

wherein $R^1$ and $R^2$ have the same meanings as defined above, with a culture of a microorganism belonging to the genus Rhodococcus, Bacillus, Brevibacterium or Gordona and being capable of stereoselectively diolating a double bond in ring A, or with said microorganism itself, or with a treated material from said microorganism.
2. The process according to item 1 above wherein the microorganism capable of stereoselectively diolating a double bond in ring A is a microorganism belonging to the genus Rhodococcus.
3. The process according to item 2 above wherein the microorganism belonging to the genus Rhodococcus is *Rhodococcus rhodochrous* ATCC 21199.
4. The process according to item 2 above wherein the microorganism belonging to the genus Rhodococcus is *Rhodococcus rhodochrous* ATCC 21198.
5. The process according to item 1 above wherein the microorganism capable of stereoselectively diolating a double bond in ring A is a microorganism belonging to the genus Bacillus.
6. The process according to item 1 above wherein the microorganism capable of stereoselectively diolating a double bond in ring A is a microorganism belonging to the genus Brevibacterium.
7. The process according to item 1 above wherein the microorganism capable of stereoselectively diolating a double bond in ring A is a microorganism belonging to the genus Gordona.
8. The process according to item 1 above wherein substrate-adsorptive carriers are added to the reaction solution.
9. A process for producing optically active diols represented by the general formula (II):

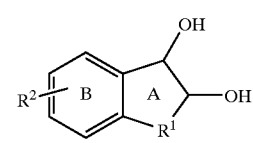

(II)

wherein $R^1$ represents $(CH_2)_n$, CH=CH, O, S or NH whereupon n is an integer of 1 to 4, and $R^2$ represents hydrogen, $C_{1-6}$ alkyl, $C_{1-6}$ alkoxy, $(C_{1-6}$ alkoxy)-carbonyl, hydroxy, carboxy, halogen, nitro or amino, which comprises treating compounds represented by the general formula (I):

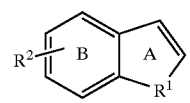

(I)

wherein $R^1$ and $R^2$ have the same meanings as defined above, with a culture of *Mortierella vinacea*, or with said microorganism itself, or with a treated material from said microorganism.
10. The process according to item 9 above wherein substrate-adsorptive carriers are added to the reaction solution.

In the definition of each group in the compounds shown in the general formula (I) or (II), the alkyl moiety in $C_{1-6}$ alkyl, $C_{1-6}$ alkoxy and ($C_{1-6}$ alkoxy)-carbonyl may be straight-chain or branched insofar as it is alkyl containing 1 to 6 carbon atoms, and examples of such alkyl include methyl, ethyl, propyl, isopropyl, butyl, isobutyl, t-butyl, pentyl and hexyl. The halogen refers to each atom of fluorine, chlorine, bromine or iodine.

The purity of the compounds represented by the general formula (I), which are used in the present invention, is not particularly limited, and those of high purity or low purity may be used. Impurities are preferably compounds not adversely affecting the growth and existence of the microorganism and the enzyme activity, but there is no particular limit insofar as their influence is negligible.

The compounds represented by the general formula (I) are preferably those wherein $R^1$ is $(CH_2)_n$, more preferably those wherein $R^1$ is $CH_2$ or $(CH_2)_2$.

The microorganisms used in the present invention may be any microorganisms belonging to the genus Rhodococcus, Bacillus, Brevibacterium or Gordona, or *Mortierella vinacea*.

The microorganisms belonging to the genus Rhodococcus include e.g. *Rhodococcus rhodochrous* ATCC 21198, *Rhodococcus rhodochrous* ATCC 21199, *Rhodococcus ruber* JCM 3205, Rhodococcus sp. IFM 18 and *Rhodococcus globerulus* ATCC 25714.

The microorganisms belonging to the genus Bacillus include e.g. *Bacillus megaterium* IAM 1032 and *Bacillus pasteurii* ATCC 11859.

The microorganisms belonging to the genus Brevibacterium include e.g. *Brevibacterium acetylicum* ATCC 953.

The microorganisms belonging to the genus Gordana include e.g., *Gordana rubropertinctus* ATCC 27863 (equivalent to *Rhodococcus ruber* JCM 3205).

*Mortierella vinacea* includes e.g. *Mortierella vinacea* TKBC 1102.

*Rhodococcus rhodochrous* ATCC 21198, *Rhodococcus rhodochrous* ATCC 21199, *Rodococcus globerulus* ATCC 25714, *Bacillus pasteurii* ATCC 11859, *Brevibacterium acetylicum* ATCC 953 and *Gordona rubropertinctus* ATCC 27863 are stored in American Type Culture Collection (ATCC) in 12301 Parklawn Drive, Rockville, Md. 20852, U.S.A. and also appear in a catalogue.

*Rhodococcus ruber* JCM 3205 is stored in Japan Collection of Microorganisms (JCM) in the Institute of Physical and Chemical Research (RIKEN) in Hirosawa 2-1, Wako-shi, Saitama, JP and also appears in a catalogue.

Rhodococcus sp. IFM 18 is stored in Research Center for Pathogenic Fungi & Microbiol Toxicosis, Chiba University (formerly Institute of Food Microbiology) in Inohana 1-8-1, Chuo-ku, Chiba-shi, Chiba, JP and also appears in a catalogue.

*Bacillus megaterium* IAM 1032 is stored in IAM Culture Collection (IAM), Center for Cellular and Molecular Research, Institute of Molecular and Cellular Biosciences, the University of Tokyo in Yayoi 1-1-1, Bunkyo-ku, Tokyo, JP and also appears in a catalogue.

*Mortierella vinacea* TKBC 1102 is stored in TKBC Culture Collection (TKBC), Institute of Biological Science, University of Tsukuba in Tennodai 1-1-1, Tsukuba-shi, Ibaraki, JP and also appears in a catalogue.

Among the microorganisms described above, preferable microorganisms include microorganisms belonging to the genus Rhodococcus, particularly *Rhodococcus rhodochrous* such as *Rhodococcus rhodochrous* ATCC 21198 and *Rhodococcus rhodochrous* ATCC 21199.

In the present invention, the compounds of the general formula (I) above are treated with a culture (e.g. a culture liquid) of the microorganism, the microorganism itself or a treated material from the microorganism (e.g. a material from the disrupted microorganism, an extract from the microorganism, or a crude or purified enzyme from the microorganism).

As the form of this treatment reaction, mention is made of e.g. a method of directly adding the substrate, that is, the compound of the general formula (I) above, to a culture liquid of the growing or grown microorganism, a method of suspending the isolated grown microorganism in a buffer and then adding the substrate thereto, and a method of immobilizing the microorganism in a usual manner, then floating it in a stirring chamber or charging it into a column, and adding the substrate thereto.

The substrate may be added all at once, but preferably added in portions. Alternatively, a continuous reaction method of continuously adding the substrate while continuously recovering the product can also be used.

Usually, the composition of the medium for culturing the microorganism used in the present invention may be any suitable medium in which the microorganism can grow, but the following composition can be mentioned as a preferable example. That is, the carbon source is glucose, mannitol or a mixture thereof, and the nitrogen source is yeast extract, corn steep liquor, peptone, meat extract or a mixture thereof. Further, inorganic materials such as common salt and manganese sulfate are preferably added.

Culture of the microorganism used in the present invention may be conducted in a usual manner, for example at pH 5 to 9, preferably 6 to 8, at a culture temperature of 20 to 40° C., preferably 25 to 30° C., and aerobically for 24 to 72 hours, but when the reaction is conducted by adding the substrate to the culture liquid, culture may be continued for 300 hours or more.

When the reaction is conducted by adding the substrate to the culture liquid, it is preferable that oil such as soybean oil or silicon oil is added at a concentration of 5 to 50%, preferably 10 to 20%, or a carrier capable of adsorbing the substrate, for example adsorptive resin (e.g. HP-20 resin, Mitsubishi Chemical) or dried yeast (Ebios™, Asahi Beer Yakuhin), is added at a concentration of about 0.5 to 10%, preferably 1 to 5%, in order to prevent the vaporization of the substrate or to avoid the inhibition of growth by the substrate.

When the microorganism is reacted after harvested, it is preferable to use the microorganism grown by adding the compound of the general formula (I) or its reduced compound such as indene, indane, naphthalene or dihydronaphthalene as an inducer for enzyme activity during culture.

Culture is conducted preferably at a reaction temperature of 15 to 50° C., preferably 20 to 30° C. and at pH 5 to 10, preferably 6 to 8. The substrate may be added all at once, but preferably added in portions, and when added to the medium, the substrate is adjusted to a concentration in the range of 0.02 to 1.0%, after which it can be added little by little as the reaction proceeds. Further, in the case of the reaction with the microorganism or with the immobilized microorganism, the concentration of the substrate is regulated in the range of 0.1 to 1.0%, after which the substrate can be added little by little as the reaction proceeds. The reaction is conducted usually under shaking or stirring. Although the reaction time varies depending on the concentration of the substrate, the density of the microorganism and any other reaction conditions, the reaction time is preferably selected such that the reaction in the case where the substrate is added to the culture medium is finished in 100 to 300 hours or more, or the reaction with the microorganism or with the immobilized microorganism is finished in 6 to 72 hours. In respect of yield, it is preferable that while the reaction is analyzed by taking an aliquot of the reaction solution, the reaction is terminated when the reaction stops.

The reaction with the microorganism isolated after culture or with the immobilized microorganism may be conducted in a sealed vessel in which an air layer corresponding to a stoichiometrically necessary amount of oxygen is kept to prevent the vaporization of the substrate.

To recover the thus obtained optically active 1,2-diol from the reaction solution, general techniques, for example extraction with organic solvent such as ethyl acetate or isopropyl acetate, can be used. For this recovery, the microorganism may be removed by centrifugation or filtration as necessary prior to extraction of the desired product. Alternatively, after removal of the microorganism from the reaction solution, the desired product may be recovered by passing the solution through a column packed with suitable adsorptive resin (e.g. SP207 resin, Mitsubishi Chemical) and then eluting the adsorbed product with a suitable solvent such as acetonitrile and methanol.

The crude extract thus obtained is dehydrated over anhydrous sodium sulfate etc., and the solvent is removed under reduced pressure whereby crude optically active 1,2-diol can be obtained. It can be further purified by recrystallization after suspended in a solvent such as ethyl acetate or through various kinds of chromatography.

BEST MODE FOR CARRYING OUT THE INVENTION

EXAMPLE 1

A medium, pH 7.0, containing 4% mannitol, 5% dried yeast (Ebios™, Asahi Beer Yakuhin), 0.005% manganese sulfate and 0.25% defoaming agent Adekanol LG109™ (Asahi Denka Kogyo K. K.) was prepared in de-ionized water, and 2.5 L of the medium was introduced into 5-L jar fermenter and sterilized at 120° C. for 20 minutes in an autoclave.

*Rhodococcus rhodochrous* ATCC 21199 was inoculated at a density of 2.4% into the medium, while 0.2% indene was added thereto, and indene diluted at a concentration of 66% with ethanol was added continuously thereto. The culture temperature was set at 30° C., stirring at 550 rpm, and aeration at 0.5 vvm. The rate of addition of the substrate was controlled by periodically taking an aliquot of the reaction solution and measuring it for the concentration of indene by high performance liquid chromatography (HPLC), whereby the concentration of indene in the medium was adjusted to 0.2%. The concentration of indene was measured by HPLC (column, Shim-pack CLC-ODS (Shimadzu Corporation); solvent, acetonitrile/water=4/1, 40° C., 1 ml/min., 248 nm).

After 143 hours, an aliquot of the reaction solution was removed and measured by HPLC (column, Chiral-pack AD (Daicel Ltd.); solvent, hexane/ethanol=92/8, 40° C., 0.5 ml/min., 220 nm), indicating that 2.20 g/l trans-(1R,2R)-indanediol, 0.06 g/l cis-(1S,2R)-indanediol and 1.00 g/l 2-hydroxy-1-indanone had been accumulated. The added indene was 11.2 g/l in total.

After 143 hours, the culture was suspended, and the microorganism was removed from the culture liquid by centrifugation. The supernatant was applied to a column packed with about 150 g adsorptive resin SP207 (Mitsubishi Chemical), washed with water and eluted with acetonitrile.

The crude extract thus obtained was dehydrated over anhydrous sodium sulfate, concentrated, dissolved in ethyl acetate at 70° C. and crystallized at a gradually decreasing temperature to give trans-(1R,2R)-indanediol. This crystal was further recrystallized from ethyl acetate to give 2.6 g crystal.

The optical purity of the resulting optically active indanediol was measured by HPLC (column, Chiralcell OK (Daicel Ltd.); solvent, hexane/isopropanol=95/5, 40° C., 0.5 ml/min., 220 nm), indicating that it was almost 100% e.e. trans-(1R,2R)-indanediol.

Measurement of its optical rotation indicated that $[\alpha]_D$ was−28.7° (c=0.936, ethanol).

EXAMPLE 2

A medium, pH 7.0, containing 1% peptone, 0.7% meat extract, 0.5% yeast extract and 0.3% common salt was prepared in de-ionized water, and 1.9 L of the medium was introduced into a 5-L jar fermenter and sterilized at 120° C. for 20 minutes in an autoclave. Thereafter, 150 g/300 ml glucose separately sterilized in an autoclave was added thereto.

*Rhodococcus rhodochrous* ATCC 21199 was inoculated at a density of 2.4% into the medium and cultured in the same manner as in Example 1.

After 24 hours, about 25 g HP-20 resin (Mitsubishi Chemical) suspended in 400 ml de-ionized water and 6.25 ml defoaming agent Adekanol LG109 (Asahi Denka Kogyo K. K.) were added thereto, and further 1 ml indene was added thereto.

Thereafter, culture was continued while 1 ml indene was added at 8-hour intervals.

After 212 hours, the culture was suspended and the concentration of the product was determined by HPLC, indicating that 5.87 g/l trans-(1R,2R)-indanediol had been accumulated. The optical purify of this trans-isomer was almost 100% e.e. in chromatography.

EXAMPLE 3

A medium, pH 7.0, containing 3% corn steep liquor, 1% yeast extract and 3% glucose was prepared in de-ionized water, and 10 ml of the medium was introduced into a thick test tube and sterilized at 120° C. for 15 minutes in an autoclave.

*Rhodococcus rhodochrous* ATCC 21199 was inoculated via a loop of platinum into the medium and cultured for 49.5 hours under shaking. Thereafter, 0.01 ml indene was added thereto, and the culture was continued for additional 16 hours.

Then, the concentration of the product was determined by HPLC, indicating that 0.55 g/l trans-(1R,2R)-indanediol, 0.15 g/l cis-(1S,2R)-indanediol and 0.19 g/l 2-hydroxy-1-indanone had been accumulated. The optical purity of the trans-isomer was almost 100% e.e. in chromatography.

EXAMPLE 4

A medium, pH 7.0, containing 1% peptone, 0.7% meat extract, 0.5% yeast extract, 0.3% common salt and 3% glucose was prepared in de-ionized water, and 15 L of the medium was introduced into a 30-L jar fermenter and sterilized at 120° C. for 30 minutes.

7.5 g naphthalene dissolved in 15 ml dimethylformamide was added to the medium, and *Rhodococcus rhodochrous* ATCC 21199 was inoculated at a density of 3% into the medium and cultured at a temperature set at 30° C., stirring at 300 rpm and aeration at 0.5 vvm. After 32.25 hours, 150 g/300 ml glucose was added thereto, and the culture was continued. After 78 hours, the culture liquid was centrifuged to give 483 g microbial pellet. 0.2 g of this microbial pellet was placed in a 15 ml plastic tube and suspended in 1 ml of 0.1 M potassium phosphate buffer, pH 8.0. 0.003 ml indene was added thereto, and the tube was sealed and incubated at 28° C. for 18 hours. After reaction, the product was extracted with 1 ml ethyl acetate and analyzed by HPLC, indicating that 2.0 g/l trans-(1R,2R)-indanediol, 0.02 g/l cis-(1S,2R)-indanediol and 0.91 g/l 2-hydroxy-1-indanone had been formed. The optical purify of the trans-isomer was almost 100% e.e. in chromatography.

EXAMPLE 5

10 g of the microbial pellet obtained in Example 4 was suspended by adding 10 ml water, and 1.5 g κ-carrageenan dissolved in 40 ml water was added thereto and well mixed therewith. This mixture was charged into an injection cylinder and dropped little by little into 1 L of 0.3 M aqueous potassium chloride to give 42 g granular immobilized microorganism.

1 g of this immobilized microorganism was introduced into a 15 ml plastic tube and added to 2 ml of 0.1 M Tris-HCl buffer, pH 8.0, and 0.03 ml indene was added thereto, and the tube was sealed and incubated at 28° C. for 18.5 hours.

1 ml supernatant, which was obtained by centrifugation after reaction, was extracted with 2 ml ethyl acetate and analyzed by HPLC, indicating that 0.42 g/l trans-(1R,2R)-indanediol, 0.05 g/l cis-(1S,2R)-indanediol and 0.12 g/l 2-hydroxy-1-indanone had been formed. The optical purity of the trans-isomer was almost 100% e.e. in chromatography.

EXAMPLE 6

20 g of the microbial pellet obtained in Example 4 was suspended by adding 20 ml water, and 3 g sodium alginate dissolved in 80 ml water was added thereto and well mixed therewith. This mixture was charged into an injection cylinder and dropped little by little into 1.5 L of 0.1 M aqueous calcium chloride to give 98 g granular immobilized microorganism.

This immobilized microorganism was incubated and measured in the same manner as in Example 5. The result indicated that 0.55 g/l trans-(1R,2R)-indanediol, 0.08 g/l cis-(1S,2R)-indanediol and 0.14 g/l 2-hydroxy-1-indanone had been formed. The optical purity of the trans-isomer was almost 100% e.e. in chromatography.

EXAMPLE 7

0.5 g/l trans-(1R,2R)-dihydroxytetrahydronaphthalene was formed in the same operation as in Example 3 except that dihydronaphthalene was used in place of indene used in Example 3.

EXAMPLE 8

10 ml of a medium, pH 7.0, containing 1% peptone, 0.7% meat extract, 0.5% yeast extract, 0.3% common salt, 1% glucose and 0.25% defoaming agent Adekanol LG109 (Asahi Denka Kogyo K.K.) was introduced into a thick test tube and sterilized at 120° C. for 15 minutes in an autoclave.

Each strain shown in Table 1 was inoculated into the medium and cultured at 28° C. under shaking. After 19 hours, 0.03 ml indene was added thereto, and the shake culture was further continued. After 40 hours in total, the reaction was terminated, and the product was extracted with ethyl acetate and analyzed. The results are shown in Table 1.

TABLE 1

| Strain | Optical Purity (% e.e.) | Steric Configuration |
|---|---|---|
| Rhodococcus rhodochrous ATCC 21198 | 100 | 1S, 2R |
| Rhodococcus sp. IFM 18 | 93 | 1R, 2S |
| Rhodococcus globerulus ATCC 25714 | 45 | 1R, 2S |
| Gordona rubropertinctus ATCC 27863 | 93 | 1R, 2S |
| Bacillus megaterium IAM 1032 | 13 | 1S, 2R |
| Bacillus pasteurii ATCC 11859 | 7 | 1S, 2R |
| Brevibacterium acetylicum ATCC 953 | 100 | 1S, 2R |

EXAMPLE 9

10 ml medium, pH 7.0, containing 2% malt extract, 2% glucose and 0.1% peptone was introduced into a thick test tube and sterilized at 120° C. for 15 minutes in an autoclave.

The strain shown in Table 2 was inoculated into the medium and cultured at 25° C. under shaking. After 68 hours, 0.03 ml indene was added thereto, and the shake culture was further continued. The reaction was terminated after 89 hours in total, and the product was extracted with ethyl acetate and analyzed. The result is shown in Table 2.

TABLE 2

| Strain | Optical Purity (% e.e.) | Steric Configuration |
|---|---|---|
| Mortierella vinacea TKBC 1102 | 35 | 1S, 2R |

INDUSTRIAL APPLICABILITY

The optically active 1,2-diols produced according to the process of the present invention are useful as various pharmaceutical preparations, optically active, biologically active substances, and intermediates of their derivatives.

What is claimed is:

1. A process for producing an optically active diol of the formula (II):

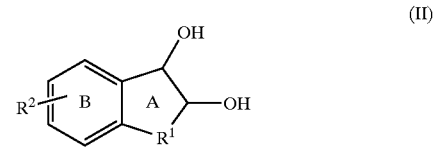

(II)

wherein $R^1$ is $(CH_2)_n$, CH=CH, O, S or NH whereupon n is an integer of 1 to 4, and $R^2$ is hydrogen, $C_{1-6}$ alkyl, $C_{1-6}$ alkoxy, ($C_{1-6}$ alkoxy)-carbonyl, hydroxy, carboxy, halogen, nitro or amino, which comprises treating a compound of the formula (I):

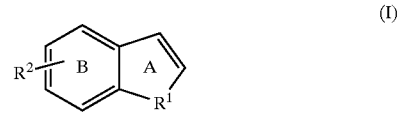

(I)

wherein $R^1$ and $R^2$ have the same meanings as defined above, with a culture of a microorganism belonging to the genus Rhodococcus, Bacillus, or Brevibacterium and being capable of stereoselectively diolating a double bond in ring A, or with said microorganism itself, or with a crude or purified enzyme from said microorganism; and recovering the optically active diol; wherein the microorganism belonging to the genus Rhodococcus is selected from the group consisting of *Rhodococcus rhodochrous* ATCC 21198, *Rhodococcus rhodochrous* ATCC 21199, *Rhodococcus ruber* JCM 3205, Rhodococcus sp. IFM 18, and *Rhodococcus globerulus* ATCC 25714; and wherein the microorganism belonging to the genus Bacillus is selected from the group consisting of *Bacillus megaterium* IAM 1032 and *Bacillus pasteurii* ATCC 11859.

2. The process according to claim 1 wherein the microorganism capable of stereoselectively diolating a double bond in ring A is a microorganism belonging to the genus Rhodococcus and is selected from the group consisting of *Rhodococcus rhodochrous* ATCC 21198, *Rhodococcus rhodochrous* ATCC 21199, *Rhodococcus ruber* JCM 3205, Rhodococcus sp. IFM 18, and *Rhodococcus globerulus* ATCC 25714.

3. The process according to claim 2 wherein the microorganism belonging to the genus Rhodococcus is *Rhodococcus rhodochrous* ATCC 21199.

4. The process according to claim 2 wherein the microorganism belonging to the genus Rhodococcus is *Rhodococcus rhodochrous* ATCC 21198.

5. The process according to claim 1 wherein the microorganism capable of stereoselectively diolating a double bond in ring A is a microorganism belonging to the genus Bacillus and is selected from the group consisting of *Bacillus megaterium* IAM 1032 and *Bacillus pasteurii* ATCC 11859.

6. The process according to claim 1 wherein the microorganism capable of stereoselectively diolating a double bond in ring A is a microorganism belonging to the genus Brevibacterium.

7. The process according to claim 1 wherein substrate-adsorptive carriers are added to the reaction solution.

8. A process for producing an optically active diol of the formula (II):

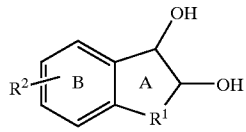

(II)

wherein $R^1$ is $(CH_2)_n$, CH=CH, O, S or NH whereupon n is an integer of 1 to 4, and $R^2$ is hydrogen, $C_{1-6}$ alkyl, $C_{1-6}$ alkoxy, ($C_{1-6}$ alkoxy)-carbonyl, hydroxy, carboxy, halogen, nitro or amino, which comprises treating a compound of the formula (I):

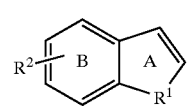

(I)

wherein $R^1$ and $R^2$ have the same meanings as defined above, with a culture of *Mortierella vinacea*, or with said microorganism itself, or with a crude or purified enzyme from said microorganism; and recovering the optically active diol.

9. The process according to claim 8 wherein substrate-adsorptive carriers are added to the reaction solution.

10. The process according to claim 6, wherein the microorganism belonging to the genus Brevibacterium is *Brevibacterium acetylicum* ATCC 953.

11. The process according to claim 1, wherein the compound of formula (I) is indene.

12. The process according to claim 2, wherein the compound of formula (I) is indene.

13. The process according to claim 3, wherein the compound of formula (I) is indene and the diol of formula (II) is trans-(1R,2R)-indanediol.

14. The process according to claim 4, wherein the compound of formula (I) is indene and the diol of formula (II) is cis-(1S,2R)-indanediol.

15. The process according to claim 9, wherein the compound of formula (I) is indene.

* * * * *